United States Patent
Chen et al.

(10) Patent No.: US 6,747,105 B2
(45) Date of Patent: Jun. 8, 2004

(54) BIS-SCHIFF BASE LIGAND-CONTAINING MONO-METALLOCENE OLEFIN POLYMERIZATION CATALYST, ITS PREPARATION PROCESS AND APPLICATION

(75) Inventors: Wei Chen, Beijing (CN); Yanlong Qian, Shanghai (CN); Gang Zheng, Beijing (CN); Bing Lian, Shanghai (CN); Jiling Huang, Shanghai (CN)

(73) Assignees: China Petroleum & Chemical Corporation, Beijing (CN); Research Institute of Petroleum Processing, Sinopec, Beijing (CN); East China University of Science and Technology, Shanghai (CN)

( * ) Notice: Subject to any disclaimer, the term of this patent is extended or adjusted under 35 U.S.C. 154(b) by 46 days.

(21) Appl. No.: 10/256,028

(22) Filed: Sep. 27, 2002

(65) Prior Publication Data

US 2003/0096927 A1 May 22, 2003

(30) Foreign Application Priority Data

Sep. 27, 2001 (CN) .......................... 01141472 A

(51) Int. Cl.⁷ .............................. C08F 4/64; C08F 4/642
(52) U.S. Cl. ...................... 526/160; 526/161; 526/172; 526/943; 502/103; 502/104; 502/117; 502/155; 502/167; 556/34; 556/52; 556/54; 556/56
(58) Field of Search ................................ 526/160, 161, 526/172, 943; 502/104, 117, 155, 167, 103; 556/34, 52, 54, 56

(56) References Cited

U.S. PATENT DOCUMENTS

| 5,502,125 A | 3/1996 | Bordeianu et al. |
| 5,637,660 A | 6/1997 | Nagy et al. |
| 5,811,379 A | 9/1998 | Rossi et al. |

FOREIGN PATENT DOCUMENTS

| EP | 0874005 A1 | 10/1998 |
| EP | 874 005 A1 * | 10/1998 |
| WO | WO 9748736 | 12/1997 |

OTHER PUBLICATIONS

George J. P. Britovsek et al., "The Search for New–Generation Olefin Polymerization Catalysts: Life beyond Metallocenes" *Angew. Chem. Int. Ed.* vol. 38, Issue 4, 1999 pp. 429–447.

* cited by examiner

Primary Examiner—Roberto Rabago
(74) Attorney, Agent, or Firm—Birch, Stewart, Kolasch & Birch, LLP

(57) ABSTRACT

A catalyst for olefin polymerization having the following structural formula (I):

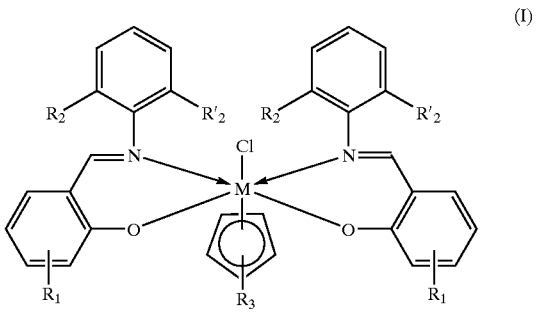

wherein $R_1$ is selected from the group consisting of hydrogen, $C_1$–$C_{12}$ alkyl, $C_1$–$C_{12}$ alkoxy, or $C_6$–$C_{12}$ aryl, $R_2$ and $R_2'$ are respectively selected from hydrogen and $C_1$–$C_4$ alkyl, $R_3$ is selected from the group consisting of hydrogen, $C_1$–$C_{12}$ alkyl, $C_1$–$C_{12}$ alkoxy and $C_6$–$C_{12}$ aryl, and M is selected from Ti, Zr, and Hf The catalyst is suitable for olefin polymerization to yield polymerized products with high molecular weight and high insertion rate of comonomers.

10 Claims, No Drawings

BIS-SCHIFF BASE LIGAND-CONTAINING MONO-METALLOCENE OLEFIN POLYMERIZATION CATALYST, ITS PREPARATION PROCESS AND APPLICATION

BACKGROUND OF THE INVENTION

The present invention relates to an olefin polymerization catalyst, its preparation process and application thereof In particular this invention relates to a bis-Schiff base ligand-containing transition metal compound, its preparation process and a process for homopolymerization or copolymerization of olefins with said compound as a major catalyst.

In the field of olefin polymerization, non-metallocene olefin polymerization catalysts exhibit certain advantages in some aspects over metallocene olefin polymerization catalysts, e.g., a much wider range of the ligand for synthesizing the catalyst, capability of some complexes to catalyze the copolymerization of polar monomers with α-olefins, capability to catalyze the oligomerization of ethylene by changing the substitution group of the ligand, and so on. V. C. Gibson (Angew. Chem, Int. Ed. 1999, 38 p428) comprehensively summarizes various catalytic systems for non-metallocene olefin polymerization, wherein the active center metal involves groups IIIB–XIB transition metals. CN1225645A discloses a post-transition metal catalyst for olefin polymerization formed by a bidentate ligand such as an imide and a central metal being selected from Groups IIIB–XIIB metals.

EP0874005A discloses a bis-schiff base [N,O]-coordinated olefin polymerization catalytic system for the first time, wherein the metal element M is selected from IIIB–XIB metals. The disclosed non-bridge complex has the following structural formula;

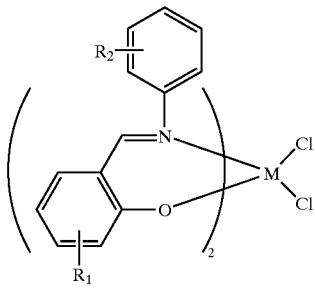

wherein $R_1$ is selected from hydrogen, halogen, and alkyl. This patent application especially points out that the substitution group adjacent to the hydroxyl is preferably halogen or $C_3$–$C_{20}$ branched alkyl if there is no substituent or the substituent which is a smaller alkyl such as methyl, ethyl and the like at this position, the polymerization activity of the system is low. This type of catalyst has major advantages of providing a same catalytic activity compared to that of an ordinary metallocene for the catalytic polymerization of olefins, and resulting in much higher molecular weight of the obtained polyethylene with broader range of distribution of the molecular weight as compared to the polyethylene derived with a metallocene catalyst. The shortcomings of such catalyst exists in that the copolymerization property is poor, and when it is used for the copolymerization of ethylene with α-olefins, the molecular weight decreases to a large extent and the insertion rate of the comonomer reached only less than 4 mol %.

An outstanding merit of the metallocene catalyst system lies in the possession of a very high copolymerization power, which is favorable to obtaining low-density polyethylene plastomer, even elastomer. However, the fatal weakness of the metallocene catalyst is that the molecular weight of the polymer drops so sharply along with the increasing insertion rate of the comonomer when the catalyst catalyzes the copolymerization of ethylene with α-olefins with a result that it is hard to simultaneously obtain polyethylene with both a high molecular weight and a high content of comonomer (high branching degree).

SUMMARY OF THE INVENTION

The object of the present invention is to provide a bis-Schiff base ligand-containing olefin polymerization catalyst and its preparation process.

Another object of the present invention is to provide a process for conducting olefin polymerization by using the aforesaid catalyst It has been found out through research work that the introduction of a cyclopentadienyl ligand into a bis-Schiff base ligand transition metal catalyst can yield a polyolefin product with a high molecular weight and a high content of the comonomer in the copolmerization of α-olefins. If such a catalyst is used for the copolymerization of ethylene with hexene, the molecular weight Mw of the polymerization product can attain to 570,000 when the insertion rate of hexene is 4.34 mol %.

DETAILED DESCRIPTION OF THE INVENTION

The olefin polymerization catalyst provided by the present invention has the following structural formula (I),

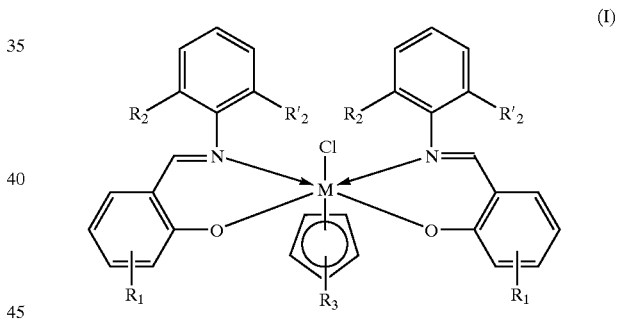

wherein $R_1$ is selected from the group consisting of hydrogen, $C_1$–$C_{12}$ alkly, $C_1$–$C_{12}$ alkoxy, and $C_6$–$C_{12}$ aryls, $R_2$ and $R_2'$ are respectively selected from hydrogen and $C_1$–$C_4$ alkyl, $R_3$ is selected from the group consisting of hydrogen, $C_1$–$C_{12}$ alkyl, $C_1$–$C_{12}$ alkoxy, and $C_6$–$C_{12}$ aryl, and M is selected from Ti, Zr and Hf.

$R_1$ in formula (I) is a substitution group on the benzene ring of salicylidene; preferably hydrogen or $C_1$–$C_6$ alkyl such as methyl, ethyl, propyl, n-butyl, iso-butyl or tert-butyl. The substitution can be at 3–6 position, preferably 3 or 5 position, i.e. the substitution is at the para- or ortho-position of the hydroxyl.

$R_2$ and $R_2'$ in formula (I) are substitution groups on the aniline ring, preferably hydrogen, methyl ethyl, propyl, iso-propyl, n-butyl, tert-butyl or iso-butyl. $R_2$ and $R_2'$ can be identical or different. If they are identical, it is preferred that both are hydrogen, methyl, ethyl, tert-butyl or iso-propyl. If they are different, it is preferred that one substitution group is hydrogen or a $C_1$–$C_4$ alkyl, and the other is a $C_1$–$C_4$ alkyl, e.g., one is hydrogen and the other is methyl, ethyl, or propyl.

R$_3$ is a substitution group on the frame of cyclopentadiene, preferably hydrogen or a C$_1$–C$_4$ alkyl such as methyl, ethyl, and more preferably hydrogen.

M is a transition metal, preferably Ti, or Zr.

The process for preparing the catalyst of the present invention comprises the following steps:

(1) Reacting a Schiff base ligand compound shown by formula (II) with an alkyl alkali metal compound in an organic medium to form an alkali metal salt of a Schiff base ligand. R$_1$ in formula (II) is selected from the group consisting of hydrogen, C$_1$–C$_{12}$ alkyl, C$_1$–C$_{12}$ alkoxy, and C$_6$–C$_{12}$ aryl, and R$_2$ and R$_2$' are selected from hydrogen and C$_1$–C$_4$ alkyl respectively

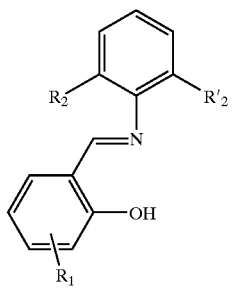

(II)

(2) Reacting the alkali metal salt of the Schiff base ligand with a cyclopentadienyl metal chloride having a formula of CpMCl$_3$ in an organic medium, removing the solvent, washing the residue with an organic solvent, filtering the resultant, and recrystallizing the filtrate. In said CpMCl$_3$, M is Ti, Zr, or Hf, Cp is a monosubstituted cyclopentadienyl, and substitution group R$_3$ is selected from the group consisting of hydrogen, C$_1$–C$_{12}$ alkyl, C$_1$–C$_{12}$ alkoxy, and C$_6$–C$_{12}$ aryl.

Step (1) relates to the reaction for preparing the alkali metal salt of the ligand, wherein the suitable reaction temperature is −78–25° C. and in particular, a low temperature should be maintained at the beginning of the reaction to prevent the rapid elevation of the reaction temperature and the formation of byproducts. Among said alkyl alkali metal compounds, alkyl lithium is preferred with butyl lithium being more preferred. In the synthesis of the ligand salt, the molar ratio of the ligand to the alkyl metal compound is 0.1–2.0:1 and the reaction time is preferably 0.1–24 hours.

The suitable temperature in reaction step (2) is −78–25° C., and the reaction time is preferably 0.5–24 hours. The molar ratio of the alkali metal salt of the Schiff base ligand to CpMCl$_3$ in the reaction is 1.0–2.0:1. Among the CpMCl$_3$ compounds, Ti is preferred for M and cyclopentadienyl is preferred for Cp.

The organic medium used in aforesaid steps (1) and (2) is selected from tetrahydrofuran and ethyl ether, preferably tetrahydrofuran. The organic solvent used for washing in step (2) is selected from the group consisting of ethyl ether, benzene, toluene, n-hexane, petroleum ether, and the mixture thereof.

The process for preparing the complex of formula (II) in step (1) comprises dehydrating condensation of the corresponding aniline compound of formula (II), such as aniline, 2,6-di-isopropyl aniline with the corresponding salicylal compound in equal mole ratio in ethanol at the reflux temperature for 0.1–10 hours; after the reaction, cooling the resultant to the room temperature, filtrating precipitated solid and removing the solvent to yield the ligand compound of formula (II).

The ligand compound preferred in the present invention includes salicylidene aniline, salicylidene 2,6-di-isopropyl aniline, salicylidene 2-isopropyl aniline, salicylidene 2,6-dimethyl aniline, salicylidene 2,6-di-ethyl aniline, 5-methyl salicylidene aniline, 5-methyl salicylidene, 6-di-isopropyl aniline, 5-ethyl salicylidene 2,6-di-isopropyl aniline, 3-isobutyl salicylidene aniline, and 3-tert-butyl salicylidene aniline.

Said CpMCl$_3$ compound in step (2) can be prepared by the following process; reacting a sodium salt of cyclopentadiene and its derivative with MCl$_4$ in equal mole in the presence of an organic medium.

The catalyst of the present invention is suitable for the homopoymerization or copolmenization of α-olefins. The polymerization process is to polymerize α-olefins or α-olefins with comonomers by using the catalyst of the present invention as a major catalyst and an alkyl aluminoxane as a cocatalyst under conditions of 10–110° C. and 0.1–1.0 MPa. The molar ratio of the aluminum in the cocatalyst to the metal in the major catalyst in polymerization is 100–1500:1, preferably 200–1000:1.

The preferred α-olefin used in polymerization is ethylene or propylene, and the preferred comonomer is butene, hexene, or octene. The polymerization may be conducted by way of bulk polymerization slurry polymerization, or gas phase polymerization.

The present invention will be further described by the following examples without limitation of the scope of the protection of the invention.

EXAMPLE 1

Preparation of di(salicylidene anilino)-(cyclopentadienyl) titanium chloride (1) Preparation of the Ligand Compound Salicylidene Aniline 24.4 g (0.2 mol) of salicylal (available from Shanghai Chemical Reagent Corp, China Medicine (Group)) and 18.63 g (0.2 mol) of aniline (available from Shanghai First Reagent Plant, China) were added into 100 ml of ethanol heated to reflux and allowed to react for 2 h with stirring, then cooled to the room temperature. Thus a great amount of crystalline was generated, which was filtered and recrystallized with 30 ml of ethanol to yield 37.5 g, yellowish-green crystalline, i.e. salicylidene aniline ligand with a yield of 95%.

(2) Preparation of the Lithium Salt of Salicylidene Aniline 2.686 g (13.6 mmol) of salicylidene aniline and 30 ml of tetrahydrofuran were added into a 100 ml Schlenk bottle, then the solution was cooled to −70° C. and 6.77 ml (2.0113 mol·L$^{-1}$, 13.6 mmol) of butyl lithium was dropped thereinto while being stirred. After completion of dropping, the temperature of the solution rose slowly to the room temperature, then said solution was stirred for 3 hours to yield the solution of the lithium salt of salicylidene aniline in tetrahydrofuran.

(3) Preparation of the Catalyst

The above solution of the lithium salt of salicylidene aniline in tetrahydrofran was cooled to −70° C. and slowly dropped into the solution of 2.987 g (13.6 mmol) of CpTiCl$_3$ in 30 ml of tetrahydrofuran at this temperature. Then the temperature of the solution rose slowly to the room temperature, afterward, said solution was stirred overnight, dried by vacuum, and 100 ml of ethyl ether was added thereinto. The resultant was filtered and the filtrate stood at −20° C. for 18 hours;. thus 1.84 g of cottony crystalline of catalyst A: di(salicylidene anilino)-(cyclopentadienyl) titanium chloride was precipitated with a yield of 25%, having the molecule formula of C$_{31}$H$_{25}$O$_2$N$_2$TiCl and the structural formula of:

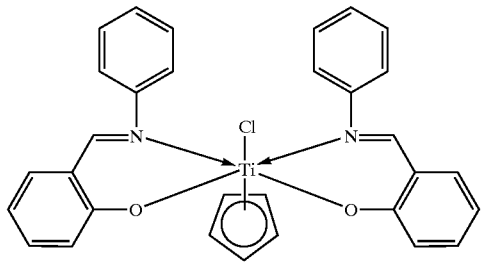
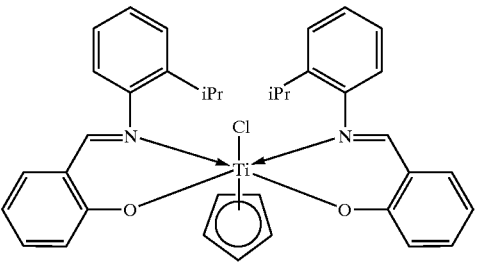

The Element Analysis Showed (by wt %):

Calculated value: C, 68.83; H, 4,67; N, 5.18

Analyzed value: C, 68.51; H, 4.87; N, 5.30

$^1$H NMR (CDCl$_3$, δ, ppm) analyzed value: 8.07–7.99 (m, 2H, CH=N), 7.42–6.05 (m, 18H, arom), 6.56 (s, 5H, C$_5$H$_5$)

M.S.: 113 (CpTi$^+$), 65 (Cp$^+$)

IR spectra: 1606(s), 1550(m), 1472(m), 1291(m), 1186 (w), 1122(w), 906(w), 860(w), 696(w)

EXAMPLE 2

Preparation of di(salicylidene ortho-isopropyl anilino-)-(cyclopentadienyl)titanium chloride (1) Preparation of the Ligand Compound Salicylidene Ortho-isopropyl Aniline The ligand compound was prepared according to the process in Example 1, except that aniline was replaced by 27 g (0.2 mol) of ortho-isopropyl aniline (available from Shanghai First Reagent Plant, China) for the reaction, 45 g of the salicylidene ortho-isopropyl aniline ligand was finally obtained with a yield of 94%.

(2) Preparation of the Lithium Salt of Salicylidene Ortho-isopropyl Aniline 2.872 g (12 mmol) of salicylidene ortho-isopropyl aniline and 30 ml of tetrahydrofuran were added into a 100 ml Schlenk bottle, then the solution was cooled to –70° C., and 5.97 ml (2.0113 mol·L$^{-1}$, 12 mmol) of butyl lithium was dropped therein to while being stirred. After completion of dropping, the temperature of the solution rose slowly to the room temperature then said solution was stirred for 3 hours to yield the solution of the lithium salt of salicylidene ortho-isopropyl aniline in tetrahydrofuran.

(3) Preparation of the Catalyst

The above solution of the lithium salt of salicylidene ortho-isopropyl aniline in tetrahydrofuran was cooled to –70° C. and slowly dropped into the solution of 2.631 g (12 mmol) of CpTiCl$_3$ in 30 ml of tetrahydrofuran at this temperature. Then the temperature of the solution rose slowly to the room temperature, afterward, said solution was stirred overnight, dried by vacuum, and 100 ml of ethyl ether was added therein to. The resultant was filtered and the filtrate stood at –40° C. for 18 hours, thus 1.68 g of cottony crystalline of catalyst B: di(salicylidene ortho-isopropyl anilino-)-(cyclopentadienyl)titanium chloride was precipitated with a yield of 45%, having the molecular formula of C$_{37}$H$_{39}$O$_2$N$_2$TiCl and the structural formula of:

The Element Anylysis Showed (by wt %):

Calculated value C, 71.09; H, 5.98; N, 4.48

Analyzed value: C, 71.01; H, 6.05; N, 4.61

$^1$H NMR (CDCl$_3$, δ, ppm) analyzed value: 8.06–7.97 (m, 2H, CH=N), 7.40–6.12 (m, 16H, arom), 6.60 (s, 5H, C$_5$H$_5$); 2.99–2.80 (m, 2H, CH(CH$_3$)$_2$), 1.20–1.05 (m, 12H, CH(CH$_3$)$_2$)

M.S.:113 (CpTi$^+$), 65 (Cp$^+$)

IR spectra: 1604(s), 1553(m), 1471(m), 1290(m), 1188 (w), 1120(w), 905(w), 868(w), 695(w)

EXAMPLE 3

Preparation of di(5-methyl salicylidene anilino-)-(cyclopentadienyl)titanium chloride (1) Preparation of the Ligand Compound 5-methyl Salicylidene Aniline The ligand compound was prepared according to the process in Example 1, except that salicylal was replaced by 27.2 g (0.2 mol) of 5-methyl salicylal (available from Shanighai Chemical Reagent Corp, China Medical (Group)) for the reaction. 40 g of the 5-methyl salicylidene aniline ligand was finally obtained with a yield of 95%.

(2) Preparation of the Lithium Salt of 5-methyl Salicylidene Aniline 2.662 g (12.6 mmol) of 5-methyl salicylidene aniline and 30 ml of tetrahydrofuran were added into a 100 ml Schlenk bottle, then the solution was cooled to –70° C. and 6.26 ml (2.0113 mol·L$^{-1}$, 12.6 mmol) of butyl lithium was dropped therein to while being stirred. After completion of dropping, the temperature of the solution rose slowly to the room temperature, then said solution was stirred for 3 hours to yield the solution of the lithium salt of 5-methyl salicylidene aniline in tetrahydrofuran.

(3) Preparation of the Catalyst

The above solution of the lithium salt of 5-methyl salicylidene aniline in tetrahydrofuran was cooled to –70° C. and slowly dropped into the solution of 2.764 g (12.6 mmol) of CpTiCl$_3$ in 30 ml of tetrahydrofuran at this temperature. Then the temperature of the solution rose slowyly to the room temperature, afterward, said solution was stirred overnight, dried by vacuum, and thereto 100 ml of ethyl ether was added. The resultant was altered and the filtrate stood at –20° C. for 18 h, thus 1.75 g of cottony crystalline of catalyst C: di(5-methyl salicylidene anilino-)-(cyclopentadienyl)titanium chloride was precipitated with a yield of 49%, having the molecular formula of C$_{32}$H$_{28}$O$_2$N$_2$TiCl and the structural formula of:

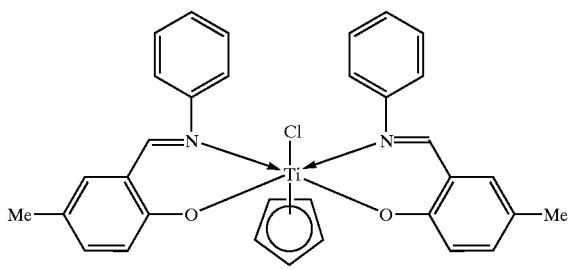

The Element Analysis of Catalyst C (by wt %) Showed:
Calculated value: C, 69.66; H, 5.15; N, 4.92
Analyzed value C, 69.50; H, 5.20; N, 4.98
$^1$H NMR (CDCl$_3$, δ, ppm) analyzed value: 8.05–7.99 (m, 2H, CH=N), 7.41–6.10 (m, 16H, arom), 6.58 (s, 5H, C$_5$H$_5$), 2.31–2.20 (m, 6H, CH$_3$)
M.S.:113 (CpTi$^+$), 65 (Cp$^+$)
IR spectral 1606(s), 1554(m), 1473(m), 1292(m), 1189 (w), 120(w), 906(w), 866(w), 696(w)

EXAMPLE 4

Preparation of di(salicylidene anilino-)-(methyl-cyclopentadienyl)titanium chloride (1) Preparation of the Lithium Salt of Salicylidene Aniline 2.367 g (12 mmol) of salicylidene aniline and 30 ml tetrahydrofuran were added into a 100 ml Schlenk bottle, then the solution was cooled to −70° C. and 3.83 ml (2.0113 mol·L$^{-1}$, 7.7 mmol) of butyl lithium was dropped thereinto while being stirred. After completion of dropping, the temperature of the solution rose slowly to the room temperature, then said solution was stirred for 3 hours to yield a solution of the lithium salt of salicylidene aniline.

(2) Preparation of the Catalyst

The above solution of the lithium salt of salicylidene aniline in tetrahydrofuran was cooled to −70° C. and slowly dropped into the solution of 2.8 (12 mmol) of MeCpTiCl$_3$ in 30 ml of tetrahydrofuran at this temperature. Then the temperature of the solution rose slowly to the room temperature, afterward, said solution, was stirred overnight, dried by vacuum, and 100 ml of ethyl ether was added thereinto. The resultant was filtered and the filtrate stood at −20° C. for 18 hours, thus 1.72 g of cottony crystalline of catalyst D: di(salicylidene anilino)-(methylcyclopeatadienyl)titanium chloride was precipitated with a yield of 52%, having the molecular formula of C$_{32}$H$_{27}$O$_2$N$_2$TiCl and the structural formula of:

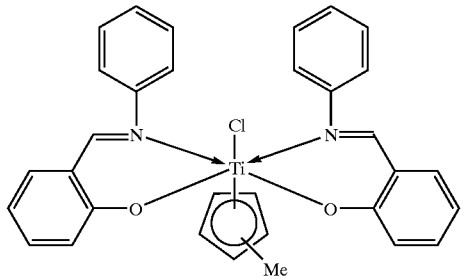

The Element Analysis Showed (by wt %):
Calculated value C, 69,26; H, 4,91; N, 5.04
Analyzed value: C, 69.10; H, 4.987; N, 5.25
$^1$H NMR (CDCl$_3$, δ, ppm) analyzed value: 8.05–7.99 (m, 2H, CH=N), 7.40–6.10 (m, 18H, arom), 6.79–6.60 (m, 2H, Cp), 6.68–6.50 (m, 2H, Cp), 2.49–2.40 (m, 3H, CH$_3$Cp)

M.S. 127(MeCpTi$^+$), 79 (MeCp$^+$)
IR spectra: 1603(s), 1553(m), 1470(m), 1292(m), 1188 (w), 1123(w), 906(w), 867(w), 697(w)

EXAMPLE 5

Preparation of di(3-tert-butyl salicylidene anilino-)-(cyclopentadienyl)titanium chloride (1) Preparation of the Ligand Compound 3-tert-butyl Salicylidene Aniline The ligand compound was prepared according to the process in Example 1, except that salicylal was replaced by 17.8 g (0.1 mol) of 3-tert-butyl salicylal for the reaction. 23.3 g of the 3-tert-butyl salicylidene aniline ligand was finally obtained with a yield of 92%.

$^1$H NMR (CDCl$_3$, 500 MHz) δ: 13.93 (br, 1H, D$_2$O, OH), 8.64 (s, 1H, CH=N), 7.46–6.96 (m, 8H, arom), 1.47 (s, 9H, C(CH$_3$)$_3$)

(2) Preparation of the Lithium Salt of 3-tert-butyl Salicylidene Aniline 2.910 ((1.5 mmol) of 3-tert-butyl salicylidene aniline and 30 ml tetraydrofuran were added into a 100 ml Schlenk bottle, then the solution was cooled to −70° C. and 5.72 ml (2.0113 mol·L$^{-1}$, 11.5 mmol) of butyl lithium was dropped thereinto while being stirred. After completion of dropping, the temperature of the solution rose slowly to the room temperature, then said solution was stirred for 3 hours to yield the solution of the lithium salt of 3-tert-butyl salicylidene aniline in tetrahydrofuran.

(3) Preparation of the Catalyst

The above solution of the lithium salt of 3-tert-butyl salicylidene aniline in tetrahydrofuran was cooled to −70° C. and slowly dropped into the solution of 2.531 g (11.5 mmol) of CpTiCl$_3$ in 30 ml of tetrahydrofuran at this temperature. Then the temperature of the solution rose slowly to the room temperature, afterward, said solution was stirred overnight, and dried by vacuum. The oily substance was extracted with ethyl ether and thus 1.85 g of red cottony crystalline of catalyst E: di(3-tert-butyl salicylidene anilino-)-(cyclopentadienyl)titanium chloride was obtained with a yield of 49%, having the molecular formula of C$_{39}$H$_{41}$O$_2$N$_2$TiCl and the structural formula of:

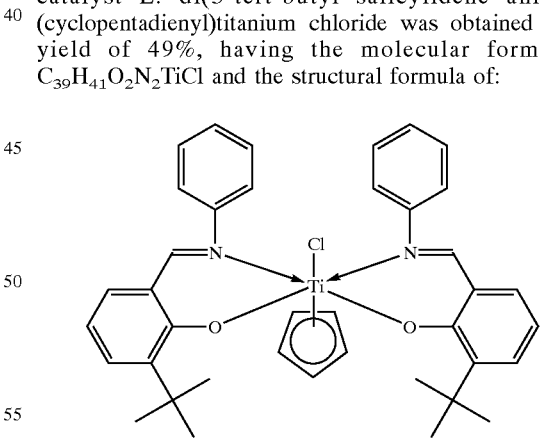

The Element Analysis of Catalyst E Showed (by wt %):
Calculated value: C, 71.71; H, 6.34; N, 4.29.
Analyzed value: C, 715.8; H, 6.45; N, 4.34
$^1$H NMR (CDCl$_3$, δ, ppm) analyzed value: 8.10–7.99 (m, 2H, CH=N), 7.44–6.05 (m, 16H, arom), 6.58 (s, 5H, C$_5$H$_5$), 1.52 (m, 18H, C(CH$_3$)$_3$)

M.S. (70 eV) m/z (%): 113 (8, CpTi$^+$), 65 (31, Cp$^+$)
IR spectra: (KBr) v: 1610, 1558, 1470, 1288, 1183, 1119, 908, 860, 698 cm$^{-1}$

EXAMPLE 6
Preparation of di(salicylidene anilino-)-(cyclopentadienyl) zirconium chloride (1) Preparation of the Lithium Salt of Salicylidene Aniline 0.678 g (3.4 mmol) of salicylidene aniline and 30 ml tetrahydrofuran were added into a 100 ml Schlenk bottle, then the solution was cooled to $-70°$ C. and 1.71 ml (2.0113 mol·L$^{-1}$, 3.4 mmol) of butyl lithium was dropped thereinto while being stirred. After completion of dropping, the temperature of the solution rose slowly to the room temperature, then said solution was stirred for 3 hours, yield the solution of the lithium salt of salicylidene aniline.

(2) Preparation of the Catalyst

The above solution of the lithium salt of salicylidene aniline in tetrahydrofuran was cooled to $-70°$ C. and slowly dropped into the solution of 1.213 g (3.4 mmol) of CpZrCl$_3$.DME (DME is ethylene glycol dimethyl ether) in 30 ml of tetrahydrofuran at this temperature. Then the temperature of the solution rose slowly to the room temperature, afterward, said solution was stirred overnight, dried by vacuum, and 30 ml of toluene was added thereinto. The resultant was filtered and the filtrate stood at $-20°$ C. for 18 hours, thus 0.62 of white crystalline of catalyst F: di(salicylidene anilino)-(cyclopentadienyl)zirconium chloride was precipitated with a yield of 62%, having the molecular formula of $C_{31}H_{25}O_2N_2ZrCl$ and the structural formula of:

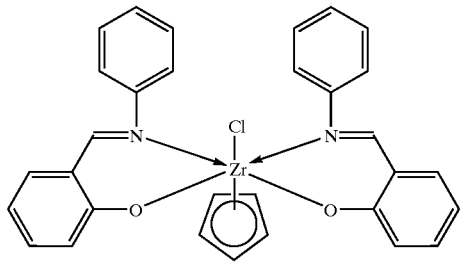

The Element Analysis Showed (by wt %);
Calculated value: C, 63.73; H, 4.32; N, 4.79
Analyzed value, C, 63.56; H, 4.52; N, 4.90

$^1$H NMR (CDCl$_3$, δ, ppm) analyzed value: 8.12–8.02 (2H, CH=N), 7.48–6.13 (m, 18H, arom), 6.59 (s, 5H, C$_5$H$_5$)

M.S.: 155(CpZr$^+$), 65 (Cp$^+$)

IR spectra: 1606(s), 1552(m), 1470(m), 1289(m), 1187 (w), 1120(w), 907(w), 856(w), 698(w)

Comparative Example 1
Synthesis of bis-Schiff Base Ligand Catalyst G 1.519 g (7.7 mmol) of salicylidene aniline and 30 ml tetrahydrofuran were added into a 100 ml Schlenk bottle, then the solution was cooled to $-70°$ C. and 3.83 ml (2.0113 mol·L$^{-1}$, 7.7 mmol) of butyl lithium was dropped thereinto while being stirred. After completion of dropping, the temperature of the solution rose slowly to the room temperature, then said solution was stirred for 3 hours to yield the solution of the lithium salt of salicylidene aniline.

The above solution of the lithium salt was slowly dropped into the solution of 1.689 g (7.7 mmol) of TiCl$_4$ in 30 ml of tetrahydrofuran at $-70°$ C. After completion of dropping, the temperature of the solution rose slowly to the room temperature, then said solution was stirred overnight, dried by vacuum, and 150 ml of ethyl ether was added thereinto. The resultant was filtered and dried by vacuum, and thus 1.2 g of solid catalyst G: di(salicylidene anilino)-titanium chloride was obtained with a yield of 61%, having the molecular formula of $C_{26}H_{20}O_2N_2TiCl_2$.

The Element Analysis Showed (by wt %):
Calculated value; C, 61.08; H, 3.95; N, 5.48
Analyzed value: C, 61.03; H, 3.94; N, 5.44

$^1$H NMR (CDCl$_3$, δ, ppm) 8.05 (s, 2H), 7.54–6.28 (m, 18H).

Comparative Example 2
Preparation of di(n-butyl cyclopentadienyl)zirconium dichloride The solution of 36.7 ml (0.09 mol) n-butyl lithium in 2.5 M hexane solution was slowly dropped into the solution of 11.0 g (0.09 mol) of n-butyl cyclopentadiene in 100 ml of tetrahydrofuran (THF) while being cooled with ice bath and stirred. After completion of dropping, the stirring was continued for 1 hours to yield a white clouding solution of n-butyl cyclopentadienyl lithium.

10.485 g (0.045 mol) of ZrCl$_4$ was slowly dropped into the above solution of n-butyl cyclopentadienyl lithium at $-78°$ C. After completion of dropping, the solution was stirred overnight to yield a red clouding solution. After 90% of the solvent was removed, the residue was dissolved in 100 ml of toluene, filtered and recrystallized to yield 12.7 g of Catalyst H: di(n-butyl cyclopentadienyl)zirconium dichloride with a yield of 70%.

EXAMPLES 7–15
Ethylene Homopolymerization was Conducted in the Following Examples.

A 250 ml glass bottle was purged with nitrogen and ethylene each for three times and 100 ml of dry toluene was added thereinto, and ethylene was added until the absorptive equilibrium. The system was heated to the reaction temperature and the catalyst and the solution of methyl aluminoxane alkoxy (MAO) in toluene were added in such amounts that the ratio of aluminum to the metal contained in the catalyst was 1000. Ethylene was added continuously and the reaction was conducted for 1 hour under the normal pressure. The reaction was stopped by adding 3 vol % solution of hydrochloric acid in ethanol. The resultant was filtered and the product was dried at 80° C. in vacuum for 3 hours to yield the polymer. The reaction temperature, catalyst activity and the polymer property in each example are shown in Table 1, wherein the weight-average molecular weight and distribution of the molecular weight were all determined by gel chromatography (GPC).

EXAMPLES 16–23
The Copolymerization of Ethylene with Hexene was Conducted in the Following Examples.

100 ml of dry toluene was added into a 250 ml glass bottle, which had been purged with nitrogen and ethylene, and ethylene was added until the absorptive equilibrium. The system was heated to 50° C., and 5 ml hexene, a small amount of catalyst and the solution of MAO in toluene were added in such amounts that the molar ratio of aluminum to the metal contained in the catalyst was 1000. Ethylene was continuously added and the reaction was stopped by adding 3 vol % solution of hydrochloric acid in ethanol after 1 hour of reaction at the normal pressure. The resultant was filtered and the product was dried at 80° C. in vacuum for 3 hours to yield the polymer. The catalyst activity and the polymer property in each example are shown in Table 2, wherein the content of hexene in the polymers was measured by $^{13}$C-NMR.

It can be seen from the data of Tables 1 and 2 that when the catalyst of the present invention was used for the homopolymerization of ethylene, the activity was higher than that of bis-Schiff base ligand Catalyst G lacking no large substitution group in the ligand used. The weight-average molecular weight and the distribution of the molecular weight of the polymers were basically the same for both situations, but the polymers had higher molecular weight than those prepared by metallocene Catalyst H. When the catalyst of the present invention was used for the copolymerization of ethylene and hexene, the polymer obtained had not only a high content of comonomer, but also a with polymer molecular weight, resulting in the performance of the polymer more suitable for further processing.

TABLE 1

| Example No. | Catalyst No. | Reaction temperature, °C. | Amount of catalyst, μmol | Activity of catalyst gPE/mol M · h | Mw | Mw/Mn |
|---|---|---|---|---|---|---|
| 7 | A | 30 | 32.0 | $4.0 \times 10^4$ | — | — |
| 8 | A | 50 | 32.0 | $4.38 \times 10^4$ | $167 \times 10^4$ | 3.2 |
| 9 | B | 50 | 30.0 | $5.1 \times 10^4$ | $160 \times 10^4$ | 3.0 |
| 10 | C | 50 | 28.5 | $3.95 \times 10^4$ | $175 \times 10^4$ | 2.95 |
| 11 | D | 50 | 29.2 | $4.5 \times 10^4$ | $170 \times 10^4$ | 2.90 |
| 12 | E | 50 | 22.0 | $1.1 \times 10^4$ | $182 \times 10^4$ | 2.87 |
| 13 | F | 50 | 15.0 | $6.1 \times 10^4$ | $130 \times 10^4$ | 2.56 |
| 14 | G | 50 | 29.7 | $0.64 \times 10^4$ | $161 \times 10^4$ | 2.85 |
| 15 | H | 50 | 10.0 | $4.1 \times 10^4$ | $11 \times 10^4$ | 2.65 |

TABLE 2

| Example No. | Catalyst No. | Reaction temperature, °C. | Amount of catalyst, μmol | Activity of catalyst, gPE/mol M · h | Mw | Mw/Mn | Hexane in polymer, mol % |
|---|---|---|---|---|---|---|---|
| 16 | A | 50 | 17.05 | $1.76 \times 10^5$ | $57 \times 10^4$ | 2.73 | 4.34 |
| 17 | B | 50 | 18.00 | $2.1 \times 10^5$ | $53 \times 10^4$ | 2.70 | 4.30 |
| 18 | C | 50 | 20.12 | $1.5 \times 10^5$ | $60 \times 10^4$ | 2.81 | 4.18 |
| 19 | D | 50 | 18.5 | $1.9 \times 10^5$ | $59 \times 10^4$ | 2.67 | 4.52 |
| 20 | E | 50 | 22 | $6.0 \times 10^5$ | $62 \times 10^4$ | 2.91 | 4.25 |
| 21 | F | 50 | 7.5 | $11 \times 10^5$ | $43 \times 10^4$ | 2.86 | 4.25 |
| 22 | G | 50 | 23.24 | $0.581 \times 10^5$ | $34 \times 10^4$ | 2.55 | 3.27 |
| 23 | H | 50 | 3.1 | $9 \times 10^5$ | $4.75 \times 10^4$ | 3.0 | 6.80 |

*M represents titanium or zirconium in Tables 1 and 2

What is claimed is:

1. A catalyst for olefin polymerization having the following structural formula (I):

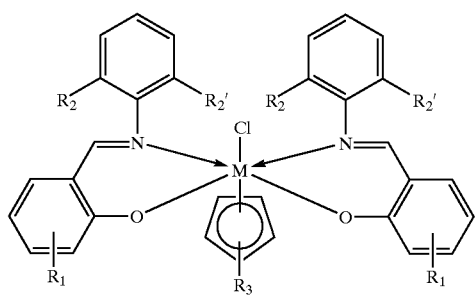

(I)

wherein $R_1$ is selected from the group consisting of hydrogen, $C_1$–$C_{12}$ alkyl, $C_1$–$C_{12}$ alkoxy, and $C_6$–$C_{12}$ aryl, $R_2$ and $R_2'$ are respectively selected from hydrogen and $C_1$–$C_4$ alkyl, $R_3$ is selected from the group consisting of hydrogen, $C_1$–$C_{12}$ alkyl, $C_1$–$C_{12}$ alkoxy, and $C_6$–$C_{12}$ aryl, and M is selected from Ti, Zr and Hf.

2. The catalyst according to claim 1, characterized in that $R_1$ in formula (I) is selected from hydrogen and $C_1$–$C_6$ alkyl, $R_2$ and $R_2'$ are respectively selected from hydrogen, methyl, ethyl, propyl, iso-propyl, n-butyl, iso-butyl and tert-butyl, $R_3$ is selected from hydrogen and $C_1$–$C_4$ alkyl, and M is selected from Ti and Zr.

3. The catalyst according to claim 1 or 2, characterized in that $R_1$ in formula (I) is hydrogen, methyl, ethyl, propyl, n-butyl, iso-butyl or tert-butyl, $R_2$ and $R_2'$ are respectively hydrogen, methyl, ethyl, propyl, iso-propyl or tert-butyl, $R_3$ is hydrogen, and M is Ti.

4. The catalyst according to claim 1, characterized in that the catalyst is di(salicylidene anilino-)-(cyclopentadienyl) titanium chloride, di(salicylidene ortho-isopropyl anilino-)-(cyclopentadienyl)titanium chloride, di(5-methyl salicylidene anilino-)-(cyclopentadienyl)titanium chloride, di(salicylidene anilino-)-(methyl-cyclopentadienyl)titanium chloride, di(3-tert-butyl salicylidene anilino-)-(cyclopentadienyl)titanium chloride, di(salicylidene anilino-)-(cyclopentadienyl)zirconium chloride.

5. The process for preparing the catalyst in claim 1, comprising the following steps:

(1) Reacting a Schiff base ligand compound of formula (II) with an alkyl alkali metal compound in an organic medium to form an alkali metal salt of a Schiff base ligand, $R_1$ in formula (II) is selected from the group consisting of hydrogen, $C_1$–$C_{12}$ alkyl, $C_1$–$C_{12}$ alkoxy, and $C_6$–$C_{12}$ aryl, $R_2$ and $R_2'$ are respectively selected from hydrogen and $C_1$–$C_4$ alkyl,

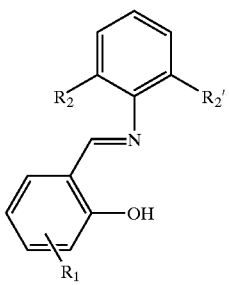

(II)

(2) Reacting the alkali metal salt of the Schiff base ligand with a cyclopentadienyl metal chloride having a formula of $CpMCl_3$ in an organic medium, removing the solvent, washing the residue with an organic solvent, filtering the resultant, and recrystallizing the filtrate, in said $CpMCl_3$, M is Ti, Zr, or Hf, Cp is a mono-substituted cyclopentadienyl, and substituent $R_3$ is selected from the group consisting of hydrogen, $C_1$–$C_{12}$ alkyl, $C_1$–$C_{12}$ alkoxy, and $C_6$–$C_{12}$ aryl.

6. The process according to claim 5, characterized in that the reaction temperature in step (1) is −78–25° C. and said alkyl alkali metal compound is butyl lithium.

7. The process according to claim 5, characterized in that the reaction temperature in step (2) is −78–25° C. and the $CpMCl_3$ compound is cyclopentadienyl titanium trichloride, cyclopentadienyl zirconium trichloride, or methyl cyclopentadienyl titanium trichloride in the reaction, the molar ratio of the alkali metal salt of the Schiff base ligand to $CpMCl_3$ is 1.0–2.0:1.

8. The process according to claim 5, characterized in that said organic medium is selected from tetrahydrofuran and ethyl ether, and the organic solvent, for washing in step (2) is selected from the group consisting of ethyl ether, benzene, toluene, n-hexane. petroleum ether, and their mixtures.

9. A process for the homopolymerization or copolymerization of α-olefins, characterized in that the catalyst of claim 1 is used as a major catalyst, and alkyl aluminoxane as a cocatalyst to polymerize α-olefins or copolymerize α-olefins with comonomers at 10–110° C. and 0.1–1.0 MPa, and with a molar ratio of aluminum in the promoter to the metal in the major catalyst of 100–1500:1.

10. A process according to claim 9, characterized in that the α-olefin is ethylene or propylene, and the comonomer is butene, hexene, or octene.

* * * * *